United States Patent
Underwood et al.

(10) Patent No.: US 6,864,490 B1
(45) Date of Patent: Mar. 8, 2005

(54) REFLECTOMETER DEVICE

(76) Inventors: James H. Underwood, 6680 Alhambra Ave., Martinez, CA (US) 94553; Rupert C. C. Perera, 6680 Alhambra Ave., Martinez, CA (US) 94553; Phillip J. Batson, 2836 Waterton La., Alameda, CA (US) 94501

(*) Notice: Subject to any disclaimer, the term of this patent is extended or adjusted under 35 U.S.C. 154(b) by 0 days.

(21) Appl. No.: 10/187,181

(22) Filed: Jun. 27, 2002

(51) Int. Cl.[7] .................................................. G01N 21/64
(52) U.S. Cl. ..................................... 250/461.1; 356/445
(58) Field of Search ....................... 356/445; 250/461.1, 250/462.1

(56) References Cited

U.S. PATENT DOCUMENTS

| | | | | | |
|---|---|---|---|---|---|
| 4,281,897 A | * | 8/1981 | Fletcher | ...................... | 356/434 |
| 4,285,596 A | * | 8/1981 | Landa | ......................... | 356/308 |
| 4,959,549 A | * | 9/1990 | Haub et al. | .............. | 250/461.1 |
| 5,524,364 A | * | 6/1996 | Cole et al. | ..................... | 36/29 |
| 5,528,364 A | * | 6/1996 | Koike | ......................... | 356/334 |
| 6,005,252 A | * | 12/1999 | Forrest et al. | ........... | 250/461.1 |
| 6,069,695 A | * | 5/2000 | Rohr et al. | .................. | 356/318 |
| 6,242,136 B1 | * | 6/2001 | Moore et al. | .................. | 430/5 |
| 6,496,260 B1 | * | 12/2002 | Hafeman et al. | ........... | 356/433 |
| 2002/0141536 A1 | * | 10/2002 | Richardson | ................. | 378/119 |

* cited by examiner

Primary Examiner—Zandra V. Smith
Assistant Examiner—Juan D. Valentin, II
(74) Attorney, Agent, or Firm—Theodore J. Bielen, Jr.

(57) ABSTRACT

A reflectometer device for determining the quality characteristics of an electronic chip mask blank utilizing a source of electromagnetic radiation in the extreme ultraviolet region. The source is passed to a monochrometer which includes a mirror, a rotatable grating, and an exit slit. The radiation travels to the mirror and is reflected to the grating which, in turn, provides a source of electromagnetic radiation which is essentially continuous and of a particular bandwidth. The grating is rotated to tune such source of electromagnetic radiation which is passed to the subject blank mask. Upon reflection from the mask, a detector determines the intensity of the reflected beam from the mask and translates such measurement into a determination of reflectivity.

6 Claims, 3 Drawing Sheets

REFLECTOMETER DEVICE

BACKGROUND OF THE INVENTION

The present invention relates to a novel and useful reflectometer device used to determine the quality of a mask blank used in the manufacture of electronic chips.

In the recent past, a very substantial advance of scientific techniques has been accomplished permitting the use of extreme ultraviolet (EUV) radiation in lithography process (EUVL) to manufacture electronic chips. The advantage of EULV is that chips of higher density are created, resulting in faster circuits, increased memories, and higher capacity devices, such as computers using such chips. Thus, EUVL has been identified as the most likely method for the next-generation lithography method used in production of electronic chips, since it is possible to operate such manufacturing techniques at the 50 nm node. Recent developments of multiplayer mirror coatings having high reflectivity at EUV wavelengths has heightened such possibility. For example, using the Low Defect Deposition (LDD) system, EULV masks have been produced having ultra clean multilayers and possessing a high reflectivity, e.g. greater than 60 percent at 13.4 nm.

Needless to say, operating in the 50 nm plateau or node requires a production environment utilizing optical elements of the highest quality. Consequently, each of the projection optics used in the EUVL system must possess diffraction-limited performance at the particular wavelength i.e. 13.4 nm. Thus, stringent requirements on the optical manufacturing of substrates for the reflective masks used in the EUVL process must be maintained. Great strides have been made in the optical field to produce EUV reflective masks possessing surface figure and roughness specifications to a level which allows EUVL production to take place. Further, tolerances on the multi-layer coatings of the EUVL masks are quite stringent. Small errors in coating thickness of EUVL mask also produce errors, similar to figure errors in the optics producing such masks. Coating inaccuracies introduce phase errors into the electromagnetic wavefront, which in turn degrades image quality on the wafer being produced.

The allowable error in the multi-layer coatings of the EUVL masks may be roughly calculated, although more rigorous calculation methods may be employed. However, back-of-the envelope, calculations indicate that coating variations must possess a very narrow range. For example, Rayleigh criteria states that an optical system will have a "diffraction-limited" performance if the wavefront exiting the system does not depart from sphericity by more than one quarter wavelength. In other words, the peak-to-valley deviation from sphericity must be less than $\lambda/4$. Thus, an optical system of n elements and figure areas of low spatial frequency add linearly. Each element can therefore contribute no more than $\lambda/4n$ to the wavefront error. Since a surface error of height creates a wavefront error of 2h, no single surface may possess a figure error of more than $\lambda/8n$. Finally, assuming that half of the figure errors in the system are found in the substrates themselves, the error in each multi-layer coating thickness cannot exceed $\lambda/16n$. It follows, that a 4-element projection system indicates that the multi-layer coating thickness must be controlled to a tolerance of $\lambda/64$. Where $\lambda$ equals 13.4 nm, thickness variations in a coating ($\Delta t$) must be less than 0.2 nm. Since the total thickness of the multiplayer stack of 40 bi-layers is approximately 40×68=2720 nm, the thickness variation of the coatings must be held to less than one part in $10^4$. Such tolerances have been achieved in manufacturing processes used today.

The attainment of close tolerances on coating thicknesses is due, in part, through coating technology and the availability of methods for measuring the multi-layer coatings at the operating wavelength (13.4 nm). Measuring coating thickness by visible light or mechanical method, such as profilometry, have proven insufficient since the effective period (d-spacing) of the coatings depend strongly on the optical constant in the EUV range. In addition, measurement of the coatings at the operating wavelength is essential for verification that the desired EUV reflectivity has been achieved.

In the past, synchrotron radiation, derived from a bending magnet, has proven advantageous as a source for calibration equipment at EUV wavelengths. Synchrotron radiation possesses high brightness with a smooth continuous spectrum and is slow in variation. Also, synchrotron radiation sources are very clean, by not possessing debris-emitting characteristics found in other sources, such as laser plasma or gas discharge. In addition, synchrotron radiation is usually maintained an operated by personnel who are experts in such technology. The disadvantage of synchrotron radiation is limited accessibility. In the United States of America, only one facility of synchrotron radiation is available at the present time. This means that optics employed in EUVL must be transported to such facility each time a measurement is to be made. Such a process is expensive, time consuming, and further exposes optical components to the risk of damage or contamination during transportation. Also, there is a delay in obtaining results from such measurements which further renders such system inefficient. The location of synchrotron radiation facilities at the EUVL manufacturing facilities would be impracticable since costs to establish such source are astronomical.

An in situ reflectometer device for determining the quality characteristics of mask blank in the EUVL field would be a notable advance in the electronic arts.

BRIEF SUMMARY OF THE INVENTION

In accordance with the present invention a novel and useful reflectometer device is herein provided.

The device of the present invention employs a source of electromagnetic radiation in the extreme ultraviolet region. Such source may take the form of a laser-generated beam which impinges on a target. The target may be composed of metallic material such as gold or copper. The reflecting radiation from the target is in the form of a source spectrum which is continuous between 10 and 15 nm. Such source spectrum is transferred for use in the present system.

A monochrometer receives the radiation source. Such monochrometer includes a mirror which reflects the radiation source to a rotating grating. A reflected beam from the grating passes to an exit slit.

A detector receives the electromagnetic radiation reflected from the mask blank and measures the intensity of the same. The detector may also include a beam splitter located to directly receive source radiation from the exit slit of the monochrometer. One beam from the beam splitter passes directly to the detector/comparitor while a second beam reflects from the mask blank and then passes to the comparitor. Reflectivity of the mask blank is then determined.

It may be apparent that a novel and useful reflectometer device has been hereinabove described.

It is therefore an object of the present invention to provide a reflectometer device which is useful in determining the reflectivity of a mask blank used in the EUVL process of manufacturing electronic chips.

Another object of the present invention is to provide a reflectometer device which may be located in situ where the manufacturing of electronic chips takes place to measure the quality of reflective mask blanks used in the EUVL process.

Another object of the present invention is to provide a reflectometer device for determining the quality characteristics of a EUVL mask blank which eliminates the transportation of EUVVL optics to a centrally located synchrotron based facility.

A further object of the present invention is to provide a reflectometer device for determining the reflectivity of mask blanks used in the EUVL process which determines coating thicknesses in EUVL mask blanks.

Yet another object of the present invention is to provide a reflectometer device which is used in the quality control of reflectivity mask blanks employed in the EUVL process to prevent the manufacture of unreliable chips made by such process.

Another object of the present invention is to provide a reflectometer device for determining the reflectivity of a EUVL mask blank that is relatively inexpensive to construct and maintain.

A further object of the present invention is to provide a reflectometer device for determining the quality characteristics of a mask blank used in the EUVL process which is compatible with clean environments used in the manufacturing of EUV mask blanks.

Another object of the present invention is to provide a reflectometer device which may be employed for the measurement of reflectivity in soft x-ray absorption spectroscopy as an analytical tool.

The invention possesses other objects and advantages especially as concerns particular characteristics and features thereof which will become apparent as the specification continues.

For a better understanding of the invention reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which is best taken in conjunction with the hereinabove delineated drawings.

Figure 1:
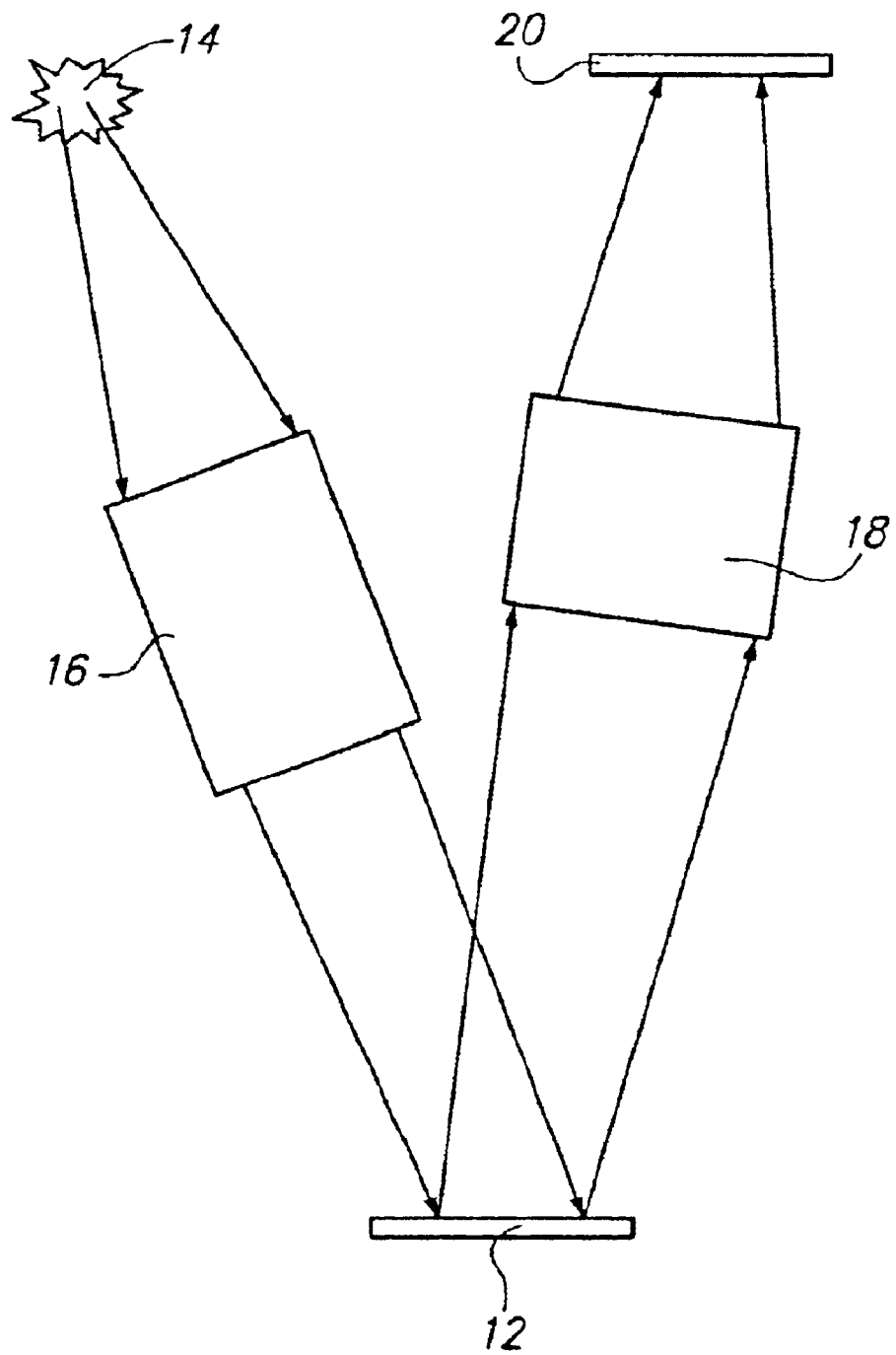
FIG. 1 is a schematic view showing the Low Defect Deposition (LDD) system for depositing ultra clean multi-layers on EUVL masks found in the prior art.
Figure 2:
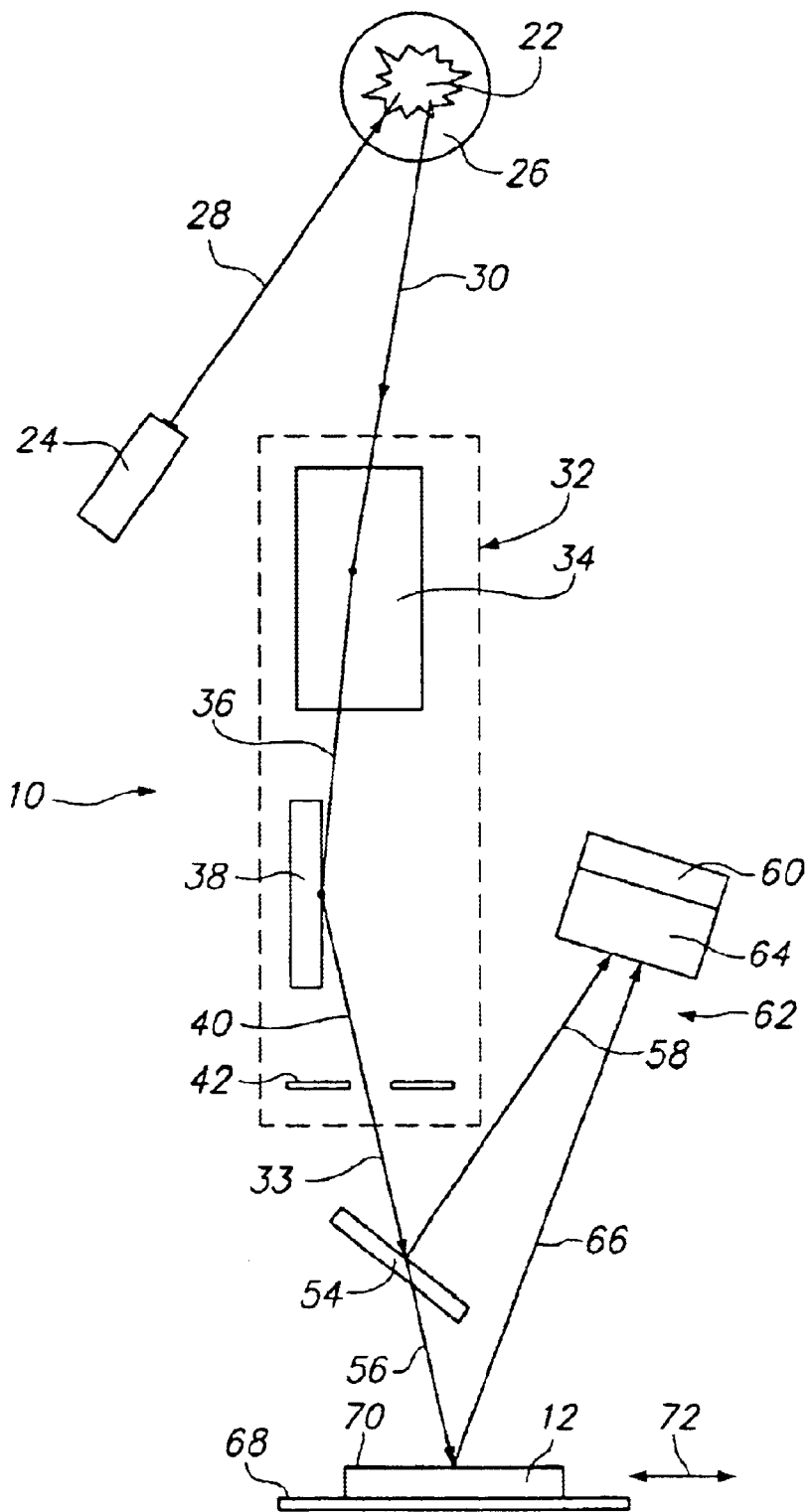
FIG. 2 is a schematic view showing the reflectometer device of the present invention in use on a EUVL mask.

The invention as a whole is depicted in the drawings by reference character 10. Reflectometer device 10, FIG. 2 is used in conjunction with a EUVL mask 12 employed in the process of manufacturing electronic chips. With reference to FIG. 1, it may be observed that the Low Defect Deposition (LDD) system is shown in which an EUV source 14 travels to condenser optics 16. The exit of the condenser optics flows to reflective mask 12 which deposits multi-layers thereupon. Reflective mask 12 is then employed through projection optics 18 to imprint a wafer 20 which is used in electronic devices such as computers.

Figure 3:
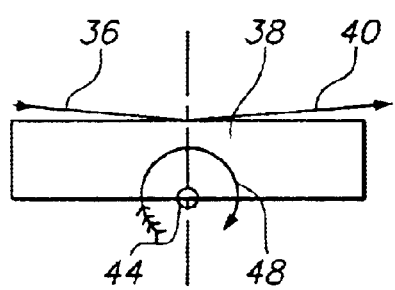
FIG. 3 is a side elevational view of the grating shown in FIG. 2.
Figure 4:
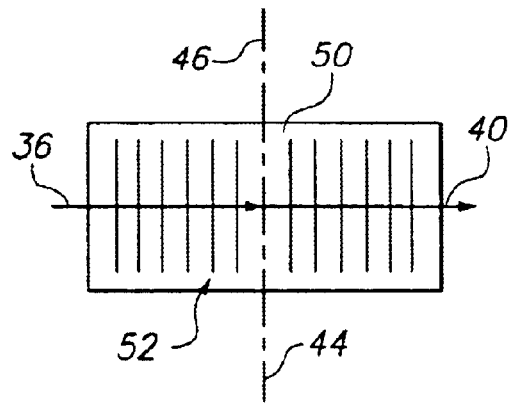
FIG. 4 is a top plan view of the grating shown in FIG. 2.

FIG. 2 depicts reflectometer device 10 which is installed in conjunction with the LDD system depicted in FIG. 1. Reflectometer device 10 is compatible with clean room environments and obviates the movement of mask 12 to a central facility such as one producing synchrotron radiation. Reflectometer device 10 includes as one of its elements a source 22 of EUV radiation. Source 22 is produced by a laser 24 such as an Nd:YAG Q-switched pulsed laser. Laser 24 produces a 30 mJ of frequency-doubled (532 nm) light with a pulse duration of 8 nanoseconds and a repetition rate of 10 hertz. Target 26, which may be formed of metal such as gold or copper, receives laser shot 28 and produces a plasma which serves as the source spectrum in the present invention. Source spectrum is essentially continuous in the EUV region between 10 and 15 nm and is denoted by beam 30 on FIG. 2. Source spectrum beam 30 is sent to monochrometer 32 to produce a narrow beam of interest, denoted by beam line 33 for eventual impingement on reflective EUVL mask 12. Monochrometer 32 includes a mirror 34 which receives EUV source beam 30 and reflects a beam 36 which passes to a rotatable grating 38. Grating 38 in turn reflects a beam 40 which passes through an exit slit 42, creating narrow beam of interest 33. FIGS. 3 and 4 detail grating 38 which rotates about a pivot 44 along axis 46. Directional arrow 48 indicates the rotational movement of grating 38. Grating surface 50 includes a plurality of grating rulings which serves to tune incident beam 36 into reflective beam 40.

After leaving exit slit 42, narrow beam of interest 33 passes through a beam splitter 54. Beam splitter allows beam 56 to pass to reflective EUVL mask 12 and also sends a beam 58 to comparitor 60. Beam splitter 54 and comparitor 60 may be deemed a detector 62 for producing values of reflectivity from reflective EUVL masks 12. In this manner, intensity of narrow beam of interest 33 originating from EUV source beam 30 is closely monitored. Fast pulse electronic means 64 measures the intensity of beam 58 and reflected beam 66 from reflective EUVL mask 12. It should be noted that mask 12 is mounted on a stage 68 which is movable in a direction parallel to surface 70 of mask 12 according to directional arrow 72. Thus, the entire surface 70 of reflective EUVL mask 12 is measured commensurate with the pulsing of laser 24. The angle of incident between fast pulse measuring means 64 and mask 12 is fixed and may be approximately 85 degrees. Of course, detector 62 may be of conventional configuration and includes a computer system known in the art.

Figure 5:
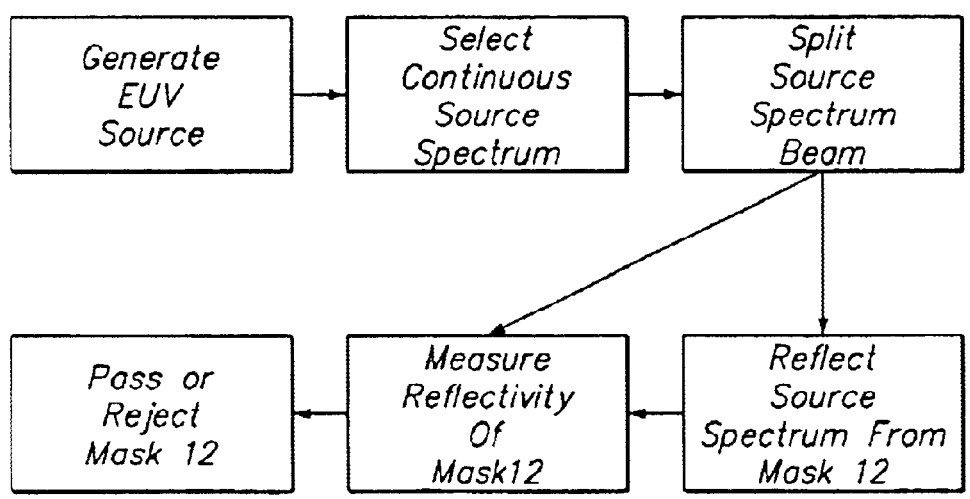
FIG. 5 is a block diagram describing the process followed in conjunction with the reflectometer device of the present invention.

In operation, the user mounts reflective EUVL mask 12 on stage 68. EUVL source 22 is generated by activating laser 24 in a pulsed manner. Target 26 generates a plasma source spectrum beam 30 which is essentially continuous in the EUV region between 10 and 15 nm. Beam 30 is passed to monochrometer 32 where it is successively reflected from mirror 34, tuning grating 38, and passed through exit slit 42. Narrow wavelength of interest 33 intercepts beam splitter 54. Beam 56 impinges on surface 70 of reflective EUV mask while beam 58 passes directly to fast pulse electronic measuring means 64. Reflected beam 66 from reflective EUVL mask 12 also passes to measuring means 64. Comparitor 60 of detector 62 then determines reflectivity of surface 70 of mask 12. FIG. 5 represents such process. After measurement of reflectivity, mask 12 is either passed or rejected according to the standards necessary to produce electronic chips using wafer 20 of FIG. 1.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A reflectometer device for determining quality characteristics of a mask blank, comprising:
   a. a source of electromagnetic radiation in the extreme ultraviolet region;
   b. a monochrometer, said monochrometer comprising a mirror, a rotatable grating, and an exit slit, electromagnetic radiation from said source of electromagnetic radiation in the extreme ultraviolet region traveling to said mirror for reflection to said rotatable grating and for reflection therefrom through said exit slit, said reflection from said grating creating a narrow beam of electromagnetic radiation in the extreme ultraviolet region, a first portion of said narrow beam of electromagnetic radiation impinging onto the blank mask in a confined area;
   c. means for rotating said grating of said monochrometer;
   d. a detector for receiving electromagnetic radiation in the extreme ultraviolet region from said impinging first portion of said narrow beam directly reflected from the mask blank and measuring the intensity of said reflected electromagnetic radiation, and for receiving a second portion of said narrow beam of electromagnetic radiation in the extreme ultraviolet region from said monochrometer and measuring the intensity of said second portion of said narrow beam; and
   e. a comparator receiving from said detector said measured intensities of said reflected first portion of said narrow beam of electromagnetic radiation and of said second portion said narrow beam of electromagnetic radiation, and determining the reflectivity of said mask blank, therefrom.

2. The device of claim 1 which further comprises a stage for supporting the mask blank and means for moving said stage to allow impingement of said first portion of said narrow beam of electromagnetic radiation along a dimension of the mask blank.

3. The device of claim 1 in which said detector further includes a beam splitter receiving said narrow beam of electromagnetic radiation in the extreme ultraviolet region from said exit slit and creating said first and second portions of said narrow beam of electromagnetic radiation in the extreme ultraviolet region.

4. The device of claim 3 which further comprises a stage for supporting mask blank and means for moving said stage to allow provide impingement of said first portion of said narrow beam of electromagnetic radiation along a dimension of the mask blank.

5. The device of claim 1 in which said source of electromagnetic radiation in the extreme ultraviolet region comprises a laser beam emanating from a laser impinging on a target to produce a source spectrum.

6. The device of claim 5 in which said laser comprises a Nd:YAG Q-switched pulsed laser.

* * * * *